United States Patent [19]

Maddux

[11] 4,174,709

[45] Nov. 20, 1979

[54] EXTENSIBLE SPLINT

[76] Inventor: Richard H. Maddux, P.O. Box 231, Whitefish, Mont. 59937

[21] Appl. No.: 862,574

[22] Filed: Dec. 20, 1977

[51] Int. Cl.² ............................................... A61F 5/04
[52] U.S. Cl. ..................................... 128/85; 128/87 R
[58] Field of Search ..................... 128/83, 84 R, 84 A, 128/84 B, 84 C, 85, 87 R

[56] References Cited

U.S. PATENT DOCUMENTS

| 1,164,956 | 12/1915 | Nourse | 128/85 |
|---|---|---|---|
| 1,843,333 | 2/1932 | McCraken | 128/83 |
| 2,024,325 | 12/1935 | Allen | 128/84 R X |
| 2,146,842 | 2/1939 | Wiessen et al. | 128/84 R |
| 2,198,908 | 4/1940 | Ellis | 128/84 R |
| 2,387,192 | 10/1945 | Straits | 128/84 R |
| 2,474,200 | 6/1949 | McBee | 128/87 B |
| 3,196,870 | 7/1965 | Sprecher et al. | 128/87 R |
| 3,284,779 | 9/1965 | Williams | 128/85 X |
| 3,680,552 | 8/1972 | Bell et al. | 128/84 C |
| 3,786,805 | 1/1974 | Tourin | 128/87 R |
| 3,906,942 | 9/1975 | Lumb, Jr. et al. | 128/85 X |
| 3,942,521 | 3/1976 | Klippel | 128/85 |

FOREIGN PATENT DOCUMENTS

| 942657 | 5/1956 | Fed. Rep. of Germany | 128/87 R |
|---|---|---|---|
| 972644 | 2/1951 | France | 128/84 R |
| 1084049 | 1/1955 | France | 128/84 R |
| 169173 | 5/1934 | Switzerland | 128/87 R |

*Primary Examiner*—E. H. Eickholt

[57] ABSTRACT

A splint for human appendages, particularly the legs, providing an articulating peripheral frame carrying a medial limb supporting element. The peripheral frame is adjustable for lineal dimension by positively acting screw means. The ends of the splint have straps for fastening to adjacent body parts to allow extension of the limb between splint ends during use. The limb support element of a species of the splint is a zipper closed pneumatic cylinder.

3 Claims, 9 Drawing Figures

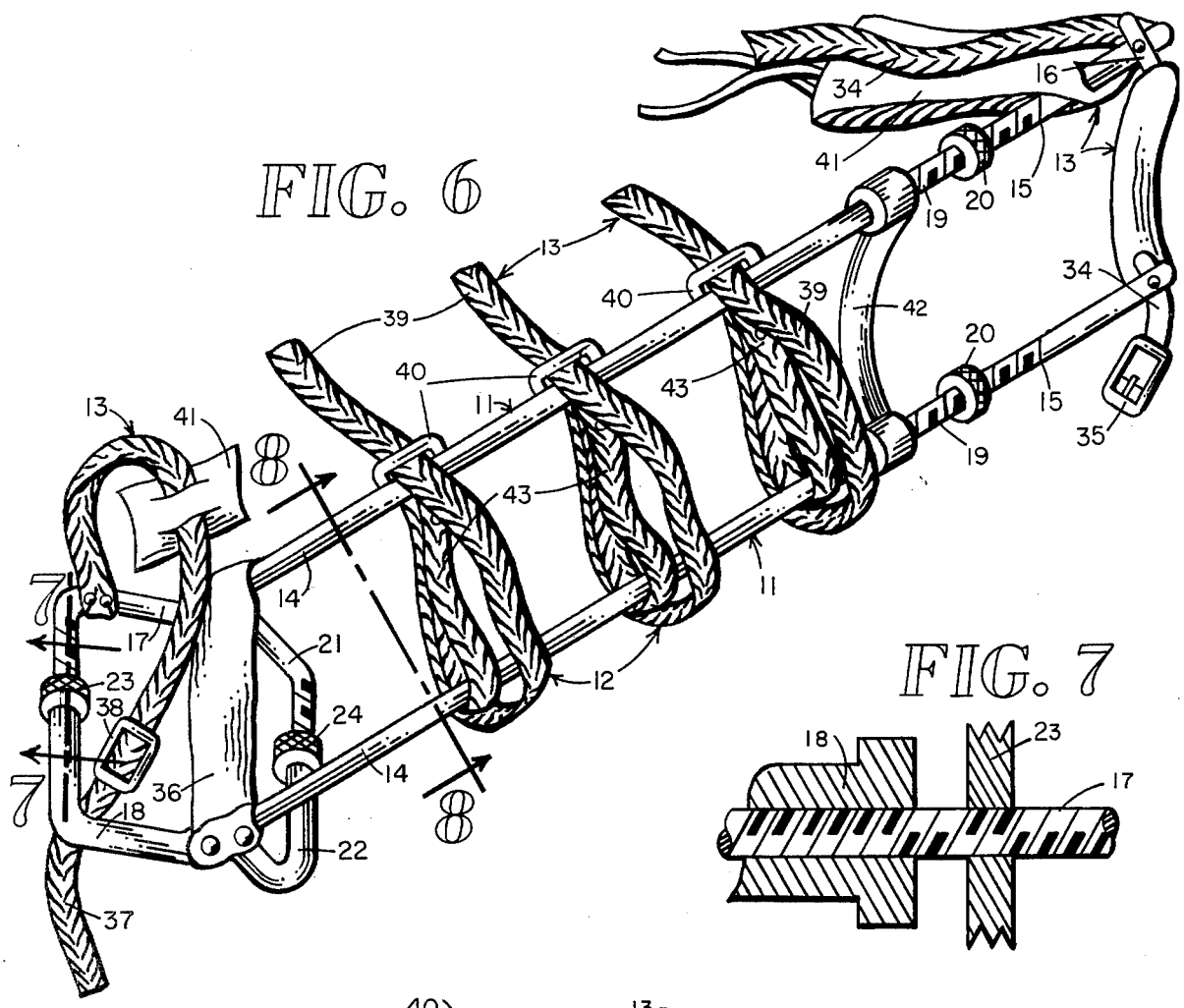
FIG. 6
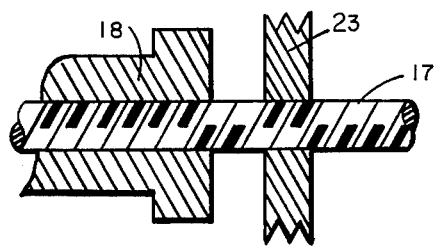
FIG. 7
FIG. 8
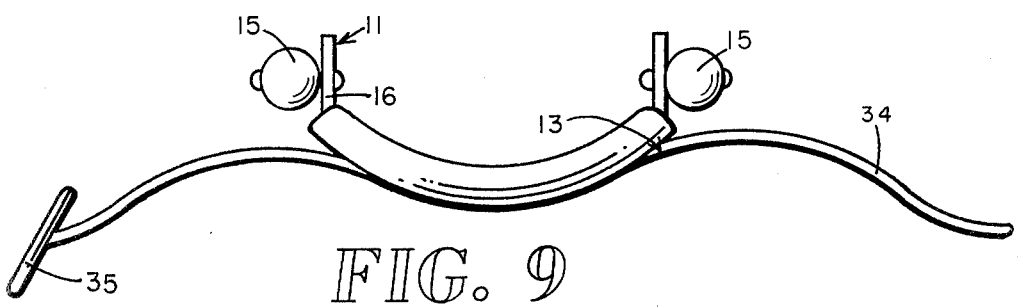
FIG. 9

EXTENSIBLE SPLINT

BACKGROUND OF THE INVENTION

RELATED APPLICATIONS

There are no applications related hereto now filed in this or any foreign country.

FIELD OF INVENTION

My invention relates generally to a splint for human appendages and more particularly to a leg splint that is adjustable extensible, especially during use.

DESCRIPTION OF PRIOR ART

In the medical and surgical arts it is oftentimes necessary to immobilize a limb of a patient, especially as in the treatment of fractures, and many splint type structures have heretofore become known for such purposes. The instant invention is such a splint, particularly for use during emergency treatment and patient transport, that provides potentiality for adjustable extension of the supported limb.

In the initial treatment of fracture type injuries of a human limb it is ordinarily desirable to immobilize the injured member, especially during transport of the victim and before a permanent fixation of the member. It again is desirable, if not necessary, to maintain the limb with some extension or to at least prevent any contraction of the muscles in it to alleviate pain and prevent further tissue or skeletal damage. If the limb should be set where complete surgical facilities are not available it is also desirable in the fixation process prior to the tradiitionl casting operation to maintain the portion of the limb about the injured area in extension. The instant invention seeks to provide apparatus having the potentiality for accomplishment of procedures of this type.

Heretofore splint devices performing at least one of the recited functions have become known and in some instances a combination of more than one of the functions have been performed by a single device. Specifically, rigid peripheral frame splints having at least two parts articulately joined have become known and these joined parts have been so articulated as to allow extension of the peripheral frame and thus establish the potentiality for establishing extension in a limb to be supported. It has become known to provide a splint with a configuration and adjustable parts that will adapt it for use on either a human arm or leg, and such multiple use splints are common in present day medical arts. It has also become known to use a pneumatic cylinder carried by a splint frame to contain and substantially imobilize a portion of a traumatized limb in a pressured fashion that tends to lessen the pain and swelling in the member during containment. The instant invention differs from this prior art by providing a splint embodying all of these features in combination and so particularized that each is operative with the others to provide functions in such combination that are greater than the total of those provided individually.

Specifically, my splint provides a sliding connection between rigid peripheral frame elements with associated mechanical screw means of extending one element relative the other to allow frame extension that is positive, easily controllable and accomplished with minimal effort. I provide an adjustable frame which, aside from its extensible features, allows adjustment of the frame members to accommodate limbs of various sizes and proportions and yet maintains its required rigidity. My splint further provides a pneumatically inflatable annular cylinder, carried by the peripheral frame for limb containment, that is completely openable and positively closable by a zipper type closure. My splint provides particularly configured end structures that may be adapted for use with either an arm or a leg on either side of the body. I also provide an open type structure that allows use of the splint frame during the setting operation on a limb by maintaining portions of the limb on opposite sides of a broken bone in extension while yet giving access about the area of the break for application of cast material.

SUMMARY OF INVENTION

My invention comprises generally an articulated peripheral splint frame carrying a medial limb restraining element.

The peripheral frame comprises opposed elongate side bars joined at their ends by cross elements, each side bar being formed with two parts extensibly joined to each other with associated screw means to extend one part relative the other. The cross member in the distal portion of the splint frame is compound and extensively joined in fashion similar to the side bars to allow lateral adjustment of the space between the two side bars. The medial, limb restraining element is an annular cylindrical structure, fastened along diametrically opposed lines to the side bars of the peripheral frame and providing a zipper type closure of the cylinder along a side element. The structure is formed of elastically resilient material to define an enclosed pneumatic chamber about a medial limb enclosing space. Limb fastening straps are provided at both distal and proximal ends of the peripheral frame to fasten that part of the splint about adjacent limb structure. Plural intermediate fastening straps are provided to encircle the side bars of the splint frame and the medial limb restraining element to aid in positionally maintaining that limb restraining element in the splint.

In creating such a splint it is:

A principal object of my invention to provide a splint with peripheral frame formed of compound elongate elements that may be mechanically adjusted to provide positive extension of the frame to allow potential extension of a supported limb.

A further object of my invention to provide such a splint that has a pneumaticly inflatable limb restraining element of annular cylindrical shape to support a traumatized limb with some pressure over a substantial area adjacent the traumatized portion to alleviate some pain and swelling.

A further object of my invention to create such a splint that has plural medial limb support bands to allow a limb to be maintained in extension in the device without enclosure by the pneumatic limb restraining element, so that the splint may be used during traditional setting operations.

A still further object of my invention to provide such a splint that is adjustable as to size to allow use with a range of limb sizes and configurations.

A still further object of my invention to provide such a splint that is of new and novel design, of rugged and durable nature, of simple and economic manufacture and otherwise well suited to the uses and purposes for which it is intended.

Other and further objects of my invention will appear from the following specification and accompanying drawings which form a part hereof. In carrying out the objects of my invention, however, it is to be understood that its essential features are susceptible of change in design and structural arrangement with only one preferred and practical embodiment being illustrated in the accompanying drawings, as is required.

BRIEF DESCRIPTION OF DRAWINGS

In the accompanying drawings which form a part hereof and wherein like numbers of reference refer to similar parts throughout:

FIG. 6 is an isometric view of a species of my splint having only strap elements to support a limb therein.

FIG. 7 is an enlarged, partial, cross-sectional view of the joint in the outer cross member of the device of FIG. 6 taken on the line 7—7 thereon in the direction indicated by the arrows.

FIG. 8 is a transverse cross-sectional view of the device of FIG. 6 taken on a line 8—8 thereon in the direction indicated by the arrows to show particularly the detailed structure of a limb fastening strap.

FIG. 9 is an orthographic view of the proximal end of the device of FIG. 6 from a viewpoint looking outwardly.

DESCRIPTION OF THE PREFERRED EMBODIMENT

Figures 1, 2, 3, 4, 5:
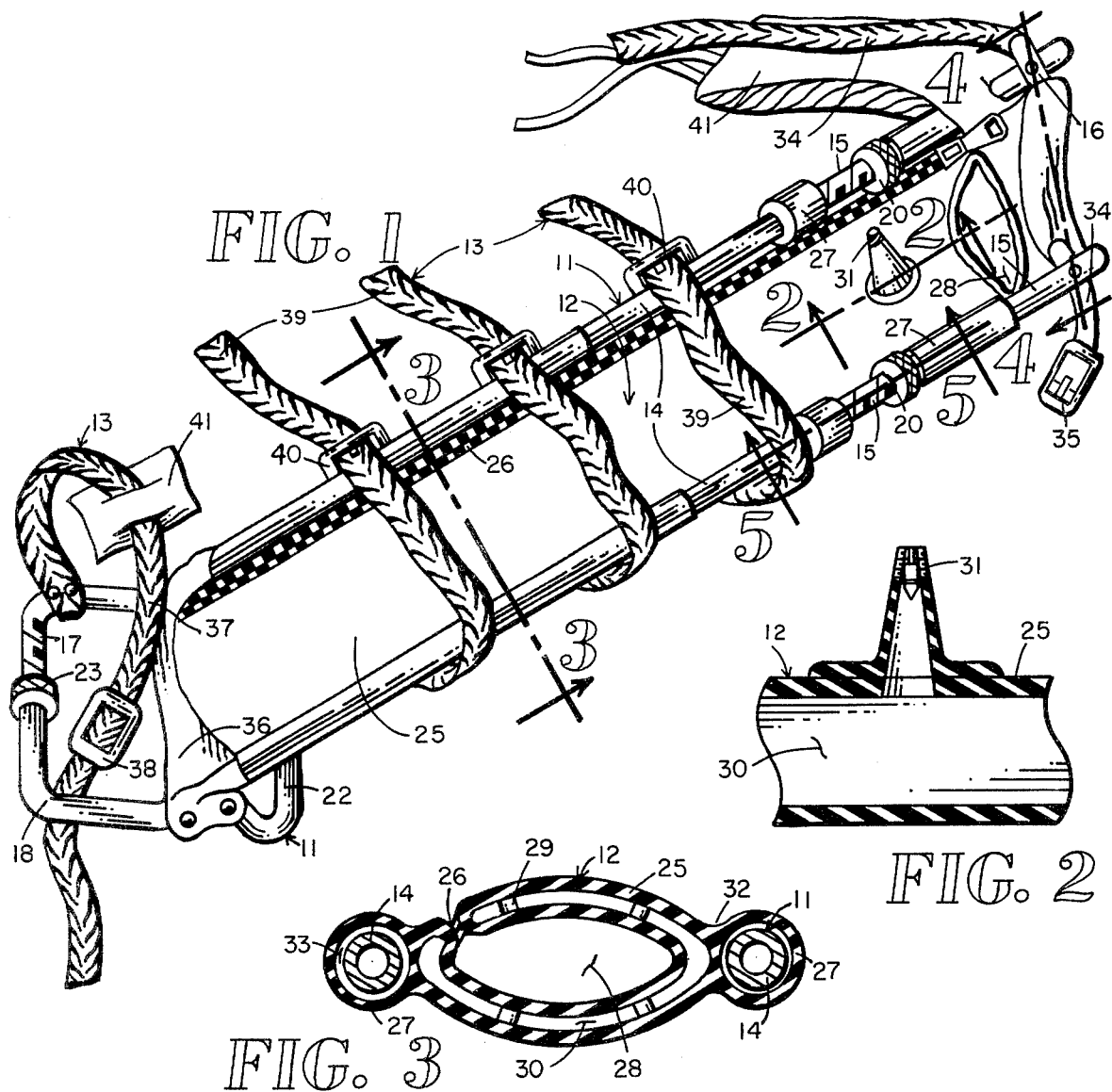
FIG. 1 is an isometric view of the principal species of my invention showing its various parts, their configuration and relationship.
FIG. 2 is an enlarged, partial cross-sectional view, of the valve device of FIG. 1 taken on the line 2—2 thereon in the direction indicated by the arrows to show the details of the valving structure.
FIG. 3 is a transverse, cross-sectional view of the device of FIG. 1 taken on the line 3—3 thereon in the direction of the arrows to show internal structural details of the limb restraining element.
FIG. 4 is a transverse, cross-sectional view through the proximal cross-member of the device of FIG. 1 taken on the line 4—4 thereon in the direction indicated by the arrows.
FIG. 5 is an enlarged partial elongate cross-sectional view of a side rod joint of the device of FIG. 1 taken on a line 5—5 thereon in the direction indicated by the arrows.

As seen especially in FIG. 1, my invention generally provides rigid, articulating peripheral split frame 11 carrying elongate limb restraining cylinder 12 and plural fastening straps 13.

The terms 'inner' and 'outer' as used in describing an end or end portion of my invention refer respectively to the end of the splint normally adjacent the most proximal part of a serviced limb and that normally adjacent the most distal part thereof. In FIGS. 1 and 6 the 'inner' end is at the right of the drawings.

Rigid peripheral frame 11 provides similar compound opposed cooperating side rods, having outer portion 14 and inner portions 15 articulately communicating with each other, joined at their inner ends by inner cross member 16 at their outer ends by outer cross member 17, 18. Preferably, though not necessarily, the frame provides in its outer end, on the side opposite cross member 17, 18 compound outer support 21, 22 structurally carried by outer end portion 14 of the side rods.

The configuration of the articulating joinder of side rods 14, 15 is shown in FIG. 5 where it is seen that outer portion 14 comprises a larger tubular element and inner member 15 a smaller rod like element so configured that portion 15 is carried within the channel defined by outer portion 14 in a slidable fit such that the two members may be moved relative each other by manual manipulation. Outer end portion 19 of inner member 15 is threaded for some distance and carries adjustment nut 20 in threaded engagement thereon so that the nut is rotated to move outwardly, inner side rod will be extended from the outer side rod 14 to cause extension of the end parts of the splint frame relative to each other. The length of the threaded portion of the outer end part of inner side rod 15 determines the amount of this extensive movement and obviously it may be nearly as long as the length of outer side rod 14.

A similar type of slidable articulating joinder is provided between outer cross member elements 17, 18 and outer support elements 21, 22; each smaller element 17, 21 is provided with threadedly engaged adjustment nuts 23, 24 to provide for lateral adjustment of the outer end part of the peripheral frame structure to accommodate various limb proportions and sizes.

Inner cross member 16 is preferably formed as a relatively flat element of appropriate cross sectional area to provide the physical rigidity and strength required of it and is mechanically joined to the inner end parts of opposed inner side rods 15 by mechanical means, preferably by riveting, as illustrated.

These rigid frame members of my splint are constructed from some sufficiently rigid, relatively light, durable material, preferably a metal such as aluminum or one of its alloys. Some plastic polymeric materials are operative for this purpose but in general those that have appropriate physical characteristics are too expensive to be economically feasible in creating a structure compatible with present day economics.

Limb restraining element 12 provides elongate, annular, cylindrical body 25, openable along one linear element by means of traditional zipper 26, and carrying opposed, cooperating frame connecting flaps 27 along diametrically opposed linear surface elements. Body 25 defines internal limb chamber 28 configured of appropriate size and shape to contain a size range of limbs. The body is formed as a double wall structure as shown especially in FIGS. 2 and 3, with plural internal separators 29 extending between opposed walls to define pneumatic chamber 30 comprising a totally enclosed chamber for containment of pressurized gas. As seen in FIG. 2, normally closed, manually and pressurably openable pneumatic valve 31 communicates from the exterior surface of body 25 to pneumatic chamber 30 to allow filling of the chamber with a pressurized gas and its deflation as required. This particular valve structure is of the type well known in the pneumatic arts. The material from which body 25 is formed is elastically resilient so that the structure, when placed about a limb to be immobilized may be inflated with pressurized gas to conform to the irregular surface of that limb carried therein, exert some pressure on the adjacent surface of that limb and maintain the limb in a supported, substantially immobile condition. The material ideally suited for this purpose and the one preferred by me is rubber, though undoubtedly other materials of the same nature, such as polymerixed plastics, would fulfill the purpose of my invention if not so well.

Frame connecting flaps 27 provide web 32 extending normally outwardly on each side from body 25 on the limb restraining element and defining in their outward portion an elongate side rod channel 33 of a size appropriate to allow outer side rod 14 to slidably pass therethrough with no more resistance than can be conveniently overcome by manual force. The limb restraining element is carried with the peripheral frame side rods in the side rod channels as illustrated in FIGS. 1 and 3. It is discontinuous over the length of body 25 to allow appropriate voids or notches therein adjacent side rod adjustment nuts 28 to allow appropriate motion of those nuts for required frame adjustments.

Fastening straps 13 maintain the splint in proper position on the body of a user and maintain a supported limb in proper position in the splint. Inner fastening strap 34 extends from structural joinder with the inner end of one inner side rod 15 to associated buckle 35 which structurally communicates with the opposed inner end of the other side rod. This strap has some length so that a limb to be supported may be supported upon inner cross member 16 with inner fastening strap 34 extending thereover to maintain the supported limb between the strap and cross member.

At the outer end of splint frame 11 flexible, strap like limb rest extends between the outer end parts of opposed outer side rods 14 to cooperate with outer support strap 37 to hold the distal part of a limb therebetween. The ends of outer limb rest 36 are mechanically fastened by riveting or similar means, to frame 11. One end of outer strap 37 is fastened to one side of the outer end portion of the splint frame preferably on one outer cross member 17, 18. The medial portion of the strap carries frictional type fastening buckle 38 so that the free end of the strap may be passed about the side of the splint frame opposite that to which it is connected and thence passed through buckle 38 to be fastened between the two outer cross members.

Medial fastening straps 39 are elongated, flexible elements carrying fastening buckles 40 at one end and having appropriate length to extend and be bastenable completely around the splint frame and limb restraining element to aid in fastening and maintaining the limb restraining element in proper position relative the frame when it is supporting a traumatized limb, especially as during transport.

Any or all of the fastening straps may have associated with them various padding and force distributing devices 41 common in the splinting arts to distribute pressures over wider areas and prevent irritation to and pain in adjacent body parts. These padding devices may be formed as an integral part of the fastening straps or may be separate and maintained thereon as desired. The fastening straps themselves are preferably formed of some reasonably flexible strong material, commonly a webbed belt fabric that is sufficiently pliable to conform to the surface contours of an adjacent supporting surface.

The species of my invention shown in FIG. 6, et seq., does not have the medial pneumatic limb restraining element, but rather only medial fastening straps somewhat modified from those principal species. This species of the invention is simpler to operate and less expensive to manufacture, and is particularly adapted to expose traumatized portions of a limb for casting while yet maintaining the limb in extension.

The basic frame of the device is the same as previously described for the primary species of my invention except an additional medial cross element 42 has been added extending between and structurally communicating with the inner end parts of outer side rods 14 to provide some additional lateral support and rigidity for this form of my invention. This cross support, again, is formed from semi-rigid strap material, preferably metal, and if so formed is preferably covered with padding of some soft pliable material. The cross member is attached to the side rods by mechanical joinder preferably by welding as illustrated. This cross piece must be somewhat flexible to allow any lateral adjustment of the outer end of the frame. Use of the cross piece is convenient but not necessary to this species of my invention, but if it be not used the splint frame is obviously the same as in the principal form.

Medial fastening straps 39 with associated buckles 40 are the same as in the principal species of the invention but each in addition has associated with it supporting straps 43 which are fastened in a band like configuration over and about the opposed side rods 14, 15 in the loose fashion illustrated, with ends fastened together and to the strap body so that the supporting strap is maintained between the frame side elements but slidable there along for lineally adjustable positioning. Each medial support strap cooperates with the associated medial fastening strap to maintain and support a limb therebetween with some force, depending upon the adjustable tension between the two straps and the size of the supported limb.

Having thusly described my invention its operation may be readily understood.

To use the principal species of my invention a splint is formed according to the foregoing specification and the various fastening straps and the limb restraining element opened. The splint is then positioned so that the limb to be supported is in the limb restraining element 12 with its traumatized portion medially located within that element. Inner fastening strap 34 is then placed over a proximal portion of the limb to be supported and fastened tightly enough to provide appropriate engagement with the portion of the limb inward of the tranumatized area. Outer fastening strap 37 is similarly fastened about the adjacent distal portion of the traumatized limb. Adjustment nuts 20 are manipulated rotatably to cause extension in the portion of the limb between the inner and outer fastening straps 34, 37. This extension is accomplished because the limb is maintained at both the inner and outer end parts of the splint by the inner and outer fastening straps and since extensive motion of the peripheral frame 11 occurs responsive to rotary motion of the adjustment nuts the limb between its supported points must necessarily be extended. Obviously for accomplishment of such limb extension the force exerted upon the limb by inner and outer fastening straps must be appropriate to prevent motion of the limb relative thereto. With such small force as is required to cause extension, however, this fastening may be readily accomplished by ordinary manual manipulation.

After the limb is placed in appropriate extension, pneumatic restraining element 12 is replaced over the upper portion of the limb to be supported and zipper 25 is fastened to provide a cylindrical structure about the traumatized area. The restraining element is then inflated with pressurized gas to an appropriate pressure of some few pound per square inch to exert some force on the contained limb but yet not cut off circulation in it or do other physiological harm. Medial fastening straps 39 are then fastened about the inflated restraining element to provide additional support of that element within the rigid peripheral frame and in this condition the contained limb is substantially immobilized and the patient may be readily transported for treatment. Normally the pneumatic pressure in the limb restraining element required to immobilize a limb and provide some pain relief is relaively small and may be provided by mouth. Higher pressure, of course, may be readily provided by any of the various pneumatic devices common in todays marketplace for dispensing pressurized gas. After inflation of the limb restraining element and if that inflation be sufficient the inner and outer limb restraining elements may be loosened or unfastened especially if they tend to disrupt normal or desirable biologic activity in the traumatized limb.

The species of my invention described is used in the same fashion as described for the principal form of the invention except that there is no pneumatic bag to completely contain the supported portion of a limb and the part of the limb about the traumatized portion may be readily worked upon while it is contained in the supporting splint. It should be noted that with the species of my invention that the medial supports may be variously positioned as desired along side rods 14, 15 to allow access to any particular portion of the limb where access may be desired, especially as for reduction and splinting.

The foregoing description of my invention is necessarily of a detailed nature so that a specific embodiment of it might be set forth as is required, but it is to be understood that various modifications of detail, rearrangement and multiplication of parts may be resorted to without departing from its spirit, essence or scope.

Having thusly described my invention, what I desire to protect by Letters Patent, and What I claim is:

1. An extensible splint for human limbs, comprising, in combination:
   a compound peripheral frame having spaced elongate, articulating side rods with associated mechanical means for adjustable extension, comprising
     the interconnecting portions of the side rods formed so that one slidably fits within the other; and
     the smaller inter-fitting end portion being threaded and carrying a threadedly engaged adjustment nut to cause extension of the larger side rod portion relative to the other smaller portion responsive to motion of the nut, said articulating side rods interconnected in inner and outer end parts by inner and outer cross members to form a peripheral splint frame, said outer cross member being compound to allow lateral adjustment of the outer portion of the splint frame and having
     two interconnecting portions formed so that one slidably fits within the other; and
     the smaller inter-fitting portion being threaded and carrying a threadedly engaged adjustment nut to cause motion of the larger inter-fitting portion relative the smaller portion responsive to motion of the nut;
   an adjustable fastening strap carried by the inner end portion of the peripheral frame to cooperate with the inner cross member to fasten therebetween a proximal part of a limb to be supported;
   an outer support strap extending between the outer end parts of the peripheral frame and an adjustable outer fastening strap extending between those same end parts and over the outer support strap to cooperate therewith to fasten a distal portion of a limb to be supported therebetween; and
   fastening means carried by the side rods of the peripheral frame to releasably fasten a human limb between the side rods.

2. The invention of claim 1 wherein the fastening means comprises:
   plural, flexible medial support straps extending between the opposed side rods of the peripheral frame so as to be adjustably positionable therealong; and
   plural adjustable fastening straps extending over and about the opposed side rods of the peripheral frame to cooperate with the medial support straps to maintain a supported limb therebetween.

3. The invention of claim 1 wherein the fastening means comprises:
   an elastically resilient medial limb restraining element formed as an elongate annular cylinder defining an internal limb chamber and an annular pneumatic chamber thereabout with opposed frame connecting flaps extending outwardly therefrom defining side rod channels to fit over and about the opposed side rods of the peripheral frame, means of opening the limb restraining element to position a limb in the internal limb chamber and means of adjustably pneumatically inflating the annular pneumatic chamber, and
   plural, adjustable medial fastening straps extending laterally over and about the peripheral frame and the limb restraining element carried thereby to aid in maintaining the limb restraining element in position relative the peripheral frame.

* * * * *